United States Patent [19]

Vaillancourt

[11] 4,402,941
[45] Sep. 6, 1983

[54] VETERINARY COMPOSITION FOR PREVENTING FELINE UROLOGICAL SYNDROME AND LITTER PRODUCT CONTAINING THE COMPOSITION

[76] Inventor: Marc Vaillancourt, 1408 11th Rang, St-Valérien, Quebec, Canada, J0H 2B0

[21] Appl. No.: 302,685

[22] Filed: Sep. 15, 1981

[51] Int. Cl.³ ..................... A61K 33/14; A61K 33/00
[52] U.S. Cl. ..................... 424/153; 424/14; 424/128; 424/127; 424/166; 424/195; 424/270; 424/280; 424/285; 424/319; 424/325
[58] Field of Search ............... 424/319, 127, 166, 153, 424/128, 195, 270, 280, 285

[56] References Cited

U.S. PATENT DOCUMENTS

| | | | |
|---|---|---|---|
| 2,783,182 | 2/1957 | Nelson | 424/274 |
| 3,281,322 | 10/1966 | Ashmead | 424/128 |
| 3,425,397 | 2/1969 | Schulein . | |
| 3,735,734 | 5/1973 | Pierce . | |
| 3,828,731 | 10/1974 | White . | |

FOREIGN PATENT DOCUMENTS

| | | |
|---|---|---|
| 486756 | 6/1938 | United Kingdom . |
| 731724 | 6/1955 | United Kingdom . |
| 758216 | 10/1956 | United Kingdom . |

OTHER PUBLICATIONS

Panel Report–Modern Vet. Practice, Jan. 1975, pp. 61-63.
Bailey–Chem. Abst., vol. 66, (1967), p. 63587e.
Animal Diseases–1956 Yearbook of Agriculture, (1956), pp. 103 and 104.
Yendt et al.–Chem. Abst., vol. 89, (1978), p. 70563x.
Gursel et al.–Chem. Abst., vol. 70, (1969), p. 36402s.
Taupitz et al., Chem. Abst., vol. 57, (1962) p. 17318g.

*Primary Examiner*—Sam Rosen
*Attorney, Agent, or Firm*—Schwartz, Jeffery, Schwaab, Mack, Blumenthal & Koch

[57] ABSTRACT

A veterinary composition for preventing feline urological syndrome in cats, comprising from 25 to 75% by weight of green plant powder, from 15 to 45% of a urine acidifying agent, from 9.5 to 28.5% by weight of a soft diuretic agent and from 0.5 to 1.5% of a calcium chelating agent, based on the total weight of the composition. A method for administering such a veterinary composition to a cat is also disclosed comprising using a veterinary litter comprising particles of wood or of wood derivatives covered with 0.1 to 4% by weight of the above veterinary composition based on the total weight of the particles. An animal using this litter composed of particles covered with an external layer of medicine impregnates its paws, part of its fur and its muzzle with medicine without noticing it and then unconsciously ingests the medicine when it cleans itself by licking its paws and fur.

16 Claims, No Drawings

VETERINARY COMPOSITION FOR PREVENTING FELINE UROLOGICAL SYNDROME AND LITTER PRODUCT CONTAINING THE COMPOSITION

BACKGROUND OF THE INVENTION

The present invention relates to a new veterinary composition for preventing feline urological syndrome in cats, such as urolithiases and related diseases encountered in cats. The invention further relates to a method of administering such a veterinary composition to the cats.

Relevant urinary diseases include uretritis, prostatis, cystitis, ureteritis, pyelonephritis, intersticial and glomerulary nephritis and stoppage of the urinary passages.

The urinary diseases encountered in cats, especially domestic cats, are responsible for about 35% of the days of hospitalization in veterinary hospitals. Sometimes these diseases are fatal to the animals. These urinary diseases are presently prevented by using expensive medicines that are both difficult and hazardous to administer.

SUMMARY OF THE INVENTION

The object of the present invention is to provide a new veterinary composition for preventing feline urological syndrome in cats, which composition permits substantial reduction of the cost involved in treating the cats, especially domestic cats, in veterinary hospitals for substantial period of time. A particularly preferred veterinary composition according to the invention comprises from 25 to 75% by weight of green plant powder, from 15 to 45% by weight of a urine acidifying agent, from 9.5 to 28.5% of a soft diuretic agent and from 0.5 to 1.5% of a calcium chelating agent, based on the total weight of the composition.

An equivalent amount of synthetic chlorophyl can be used in place of the green plant powder, which, inter alia, brings to the animal substantial amounts of carotene and other oligo-elements contained in the plants. Preferably, about 50% by weight of green plant powder is used in the composition.

Preferably also, DL-methionine is used as the urine acidifying agent. However, this compound can be replaced by ammonium chloride, ethylene diamine dihydrochloride, mandelic acid, ascorbic acid, sodium biphosphate or any other urine acidifying substance. The urine acidifying agent preferably comprises about 30% by weight of the total composition.

Sodium chloride is preferably used as the soft diuretic agent. However, use can also be made of furosemide (sold in Canada under the trademark LASIX), hydrochlorothiazide or acetazolamide (sold in Canada under the trademark DIAMOX). The diuretic agents preferably comprise about 19% by weight of the total composition.

As the calcium chelating agent, use can advantageously be made of ethylene diamine tetraacetic acid. This agent preferably comprises about 1% by weight of the composition.

In accordance with a particularly preferred embodiment of the invention, the veterinary composition comprises about 50% by weight of green plant powder, about 30% by weight of DL-methionine, about 19% by weight of sodium chloride and about 1% by weight of ethylene diamine tetraacetic acid, based on the total weight of the composition.

The veterinary composition according to the invention which results from the synergistic mixing of the four components mentioned hereinabove, has the following advantages:

it acidifies the urine;
it assists in preventing inflammation of the urinary tract;
it reduces the odor of the urine and stools of the animals;
it gives a better breath to the domestic animals;
it reduces the amount of dry substances in the urine by at least 45%; and
it helps in preventing urolithiases and the aforementioned related urinary diseases.

Another object of the present invention is to provide a new method of administering medicine to animals, and more particularly of administering the above-defined veterinary composition.

Every animal owner knows that it is very difficult to orally administer medicine to an animal. Indeed, the animal is generally panic stricken and struggles, bites, claws and spits the medicine out. If a tablet of medicine is pulverized and mixed with the animal's food or a liquid mixture is poured into its food, the animal refuses to eat or swallows only part of its meal and therefore only part of its medicine.

In order to overcome this drawback, a new veterinary litter is provided which is especially designed for preventing urolithiases and related urinary diseases in cats. This new litter comprises particles of wood or wood derivatives covered with from 0.1 to 4% by weight of the above described veterinary composition, based on the total weight of the particles.

As used herein the term "litter" means every "substance" placed in a container or tray and used as a toilet place for a domestic cat or any other animal kept in captivity.

The main advantage of the litter according to the invention, whose particles are covered with an external layer of medicine, lies in that the animal impregnates its paws, part of its fur and its muzzle with medicine without noticing it and then unconsciously ingests the medicine when it cleans itself and licks its paws and fur. In this regard, it should be noted that cats are known as very clean animals which lick themselves after urinating or passing stools.

By way of example, a domestic cat needs about 2500 $cm^3$ of litter for relieving its stool and urine in a hygienic way for a period of 3 to 4 days. This volume of litter is spread onto a surface of about 1000 $cm^2$. Taking into account that the average surface covered by the feet of a domestic cat is about 40 $cm^2$, a cat using the litter will pick up every day from 5 to 15% of medicine added to its litter.

The particles used as a substrate for the medicine to be picked up by the animal when using its litter, are preferably made of wood sawdust or shavings or of absorbent paper or of any other form of pulp. Each particle preferably has a volume of from 0.1 to 5 $cm^3$. For example, use can be made of commercially available hygienic paper rolled in small cylinders having a diameter from 0.2 to 2 cm and a length from 0.2 to 5 cm. The particles can also be given any geometrical shape. Natural sawdust or a treated sawdust from which the smaller particles have been removed, is particularly useful since sawdust is very easy to find and inexpensive to buy and is also only half the weight per volume of the ground clay conventionally used as litter. Moreover, sawdust absorbs 50% more water than the same volume of litter made of ground clay. A paper paste treated with sodium polyacrylate in order to increase by 30 times its liquid absorption capacity can also be used.

A very advantageous characteristics of the litter according to the invention resides in that its particles are much less dusty than the ground clay particles used in conventional litter. A small amount of the litter specifically described hereinabove by way of example has proved to be sufficient for absorbing a larger amount of cat urine and stools within the same period of time as compared to a known litter, because of its improved capacity of absorption. Additionally, the porous particles used in the litter according to the invention can advantageously carry and retain the medicine without affecting its curative properties before it is picked up and ingested by the animals.

The invention will be betteer understood from a consideration of the following, non-restrictive example.

EXAMPLE

A veterinary composition for preventing urolithiase of the urinary passages of cats was prepared by intimately mixing about 5 parts by weight of green plant powder, 3 parts by weight of DL-methionine, 1.9 part by weight of sodium chloride and 0.1 part by weight of ethylene diamine tetraacetic acid. The resulting composition was grounded into a fine powder. A thin coating of the thusly obtained powder was then applied to sawdust, by using 5 grams of powder per kilogram (or about 5000 $cm^3$) of sawdust, to give a veterinary litter that was subsequently tested with 6 domestic cats 1 to 3 years of age, including 4 males and 2 females, all sterilized (castrated or ovariohysterectomised). After an adaptation period of 2 weeks, with a "conventional litter" a sample of urine was collected from each cat and the proportion of dry material contained in each sample was measured. Thereafter, the cats were allowed to use the veterinary litter previously prepared, for a period of 3 weeks. At the expiration of the three weeks period, another sample of urine was collected from each cat and the proportion of dry material in this sample was measured. The resulting data from the tests is given in the following table:

| Cat No. | Proportion of dry material in the urine (expressed in grams per ml of urine) | |
|---|---|---|
| | Initial Solids Content of Urine | Solids Content After Three Weeks Use of Litter of Invention |
| 1 | 0.09 gm/ml | 0.02 gm/ml |
| 2 | 0.04 gm/ml | 0.04 gm/ml |
| 3 | 0.14 gm/ml | 0.03 gm/ml |
| 4 | 0.08 gm/ml | 0.07 gm/ml |
| 5 | 0.13 gm/ml | 0.07 gm/ml |
| 6 | 0.11 gm/ml | 0.05 gm/ml |
| Average: | 0.098 gm/ml | 0.048 gm/ml |

The above table shows that before using the veterinary litter according to the invention, the urine of the cats contained an average amount of 0.098 grams of dry material per milliliter of urine. After using the litter according to the invention for 3 weeks, the urine of the same cats contained an average of only 0.048 grams of dry material per milliliter of urine. In each case the proportion of dry material in the urine was determined by complete evaporation of the total urine.

Another experiment was carried out to determine the percentage of dry material in the urine by centrifugation of the urine, separation of floating material and evaporation of the sediment. Normal cats under control had a proportion of 3.33 milligrams of dry material per ml of urine while cats using the litter according to the invention had a proportion of 1.84 milligrams of dry material per ml of urine. Accordingly, it can be seen that the litter according to the invention reduces by about 45% the proportion of solid material in the urine capable of inflamming and even obstructing the urinary passages. In this regard, it should be noted that a test of cats suffering from urinary tract syndrome, showed an average proportion of solid material in the urine of about 5.61 miligrams per ml of urine.

The advantages of this new method of administering a veterinary composition to cats include
  the convalescent animal does not undergo any stress;
  the medicine is administered in a continuous and regular manner, and
  the danger of the owner of the cat being bitten or scratched is reduced.

It should be noted that this method of administering a veterinary product to an animal is not restricted to cats or to the very specific veterinary composition disclosed hereinabove. As a matter of fact, this method can also be used for administering topical or oral insecticides, antibiotics, vitamins, anovulants and any other preparations or compositions for preventing other specific diseases or any other reasons.

The foregoing embodiments have been described merely as illustrative examples of the invention and are not intended to be limiting. Since modifications of the disclosed embodiments incorporating the spirit and substance of the invention may occur to persons skilled in the art, the scope of the invention is to be limited solely with respect to the scope of the appended claims.

I claim:

1. A veterinary composition suitable for application to a substrate and for preventing feline urological syndrome in cats, comprising from 25 to 75% by weight of green plant powder, from 15 to 45% of a urine acidifying agent, from 9.5 to 28.5% by weight of a soft diuretic agent and from 0.5 to 1.5% of a calcium chelating agent, based on the total weight of the composition.

2. A veterinary composition according to claim 1, wherein the green plant powder comprises about 50% by weight based on the total weight of the composition.

3. A veterinary composition according to claim 1, wherein the urine acidifying agent is selected from the group consisting of DL-methionine, ammonium chloride, ethylene diamine dihydrochloride, mandelic acid, ascorbic acid and sodium biphosphate.

4. A veterinary composition according to claim 3, wherein the urine acidifying agent is DL-methionine.

5. A veterinary composition according to claim 1, 3 or 4, wherein the urine acidifying agent comprises about 30% by weight based on the total weight of the composition.

6. A veterinary composition according to claim 1, wherein the soft diuretic agent is selected from the group consisting of sodium chloride, furosemide, hydrochlorothiazide and acetazolamide.

7. A veterinary composition according to claim 6, wherein the soft diuretic agent is sodium chloride.

8. A veterinary composition according to claim 1, 6 or 7, wherein the soft diuretic agent comprises about 19% based on the total weight of the composition.

9. A veterinary composition according to claim 1, wherein the calcium chelating agent is ethylene diamine tetraacetic acid.

10. A veterinary composition according to claim 1 or 9, wherein the calcium chelating agent comprises about 1% by weight based on the total weight of the composition.

11. A composition according to claim 1, comprising about 50% by weight of green plant powder, about 30% by weight of DL-methionine, about 19% by weight of sodium chloride and about 1% by weight of ethylene diamine tetraacetic acid, based on the total weight of the composition.

12. A veterinary litter for preventing feline urological syndrome in cats, comprising particles of wood or wood derivative coated with from 0.1 to 4% by weight of a veterinary composition according to claim 1, based on the weight of the particles.

13. A veterinary litter according to claim 12, wherein said particles are made of wood sawdust, wood shavings or absorbent paper.

14. A veterinary litter according to claim 12 or 13 wherein each particle has a volume ranging from 0.1 to 5 cubic centimeters.

15. A veterinary litter according to claim 12, wherein the particles are coated with about 0.5% by weight of the veterinary composition, based on the total weight of the particles.

16. A veterinary litter according to claim 12, or 15, wherein said veterinary composition comprises about 50% by weight of green plant powder, about 30% by weight of DL-methionine, about 19% by weight of sodium chloride and about 1% by weight of ethylene diamine tetraacetic acid.

* * * * *